United States Patent [19]

Breyer et al.

[11] Patent Number: 4,697,595
[45] Date of Patent: Oct. 6, 1987

[54] ULTRASONICALLY MARKED CARDIAC CATHETERS

[75] Inventors: Branko Breyer; Ivo Cikes, both of Zagreb, Yugoslavia

[73] Assignee: Telectronics N.V., Curacao, Netherlands

[21] Appl. No.: 697,056

[22] Filed: Jan. 31, 1985

[30] Foreign Application Priority Data

Jul. 24, 1984 [YU] Yugoslavia ............................ 1327/84

[51] Int. Cl.⁴ ............................................. A61B 10/00
[52] U.S. Cl. ...................................... 128/660; 128/661
[58] Field of Search ............................... 128/660–663, 128/24 A

[56] References Cited

U.S. PATENT DOCUMENTS

| | | | |
|---|---|---|---|
| 3,938,502 | 2/1976 | Bom .................................. | 128/661 X |
| 4,237,729 | 12/1980 | McLeod et al. ................... | 128/663 X |
| 4,354,501 | 10/1982 | Colley et al. ..................... | 128/660 X |
| 4,407,294 | 10/1983 | Vilkomerson ...................... | 128/660 |
| 4,431,006 | 2/1984 | Trimmer et al. ................... | 128/660 |
| 4,576,177 | 3/1986 | Webster, Jr. ...................... | 128/660 |

*Primary Examiner*—Lee S. Cohen
*Assistant Examiner*—Francis J. Jaworski
*Attorney, Agent, or Firm*—Gottlieb, Rackman & Reisman

[57] ABSTRACT

The hollow cylindrical wall of the catheter is composed of flexible, electrically insulating, ultrasonically transparent material. Embedded therein are spaced tubular-shaped ultrasonic piezoelectric transducers which substantially surround the lumen. The transducers receive signals from the imaging transducer on the body surface and serve to establish catheter location within the body during a diagnostic procedure. Electrical connector leads from the transducers are embedded in the wall and connected to a signal processor which provides an output for incorporation into the display of an echocardiograph image display system.

7 Claims, 3 Drawing Figures

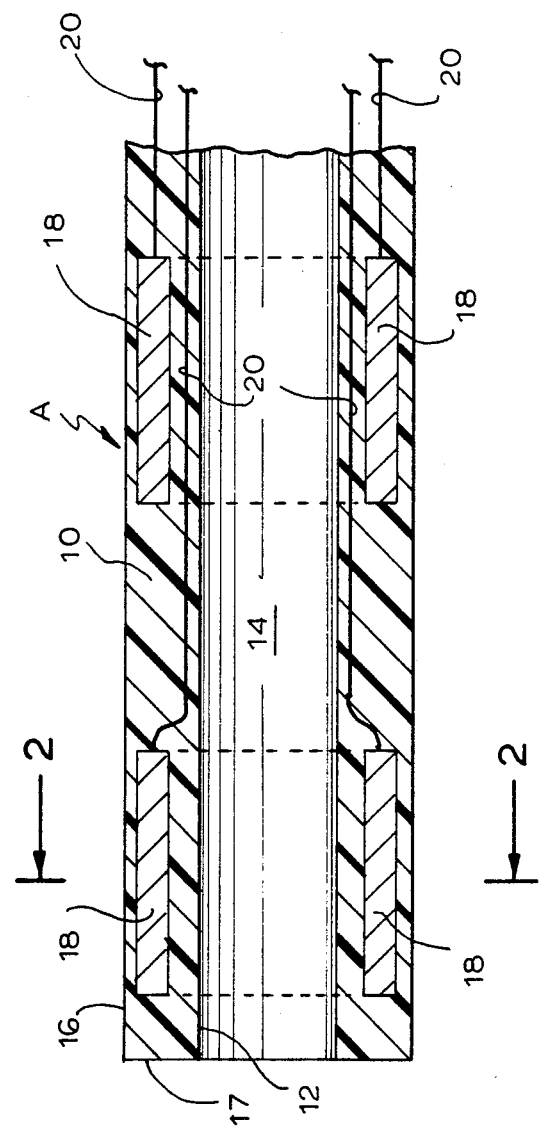
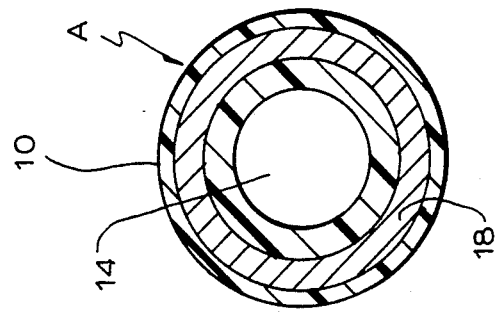

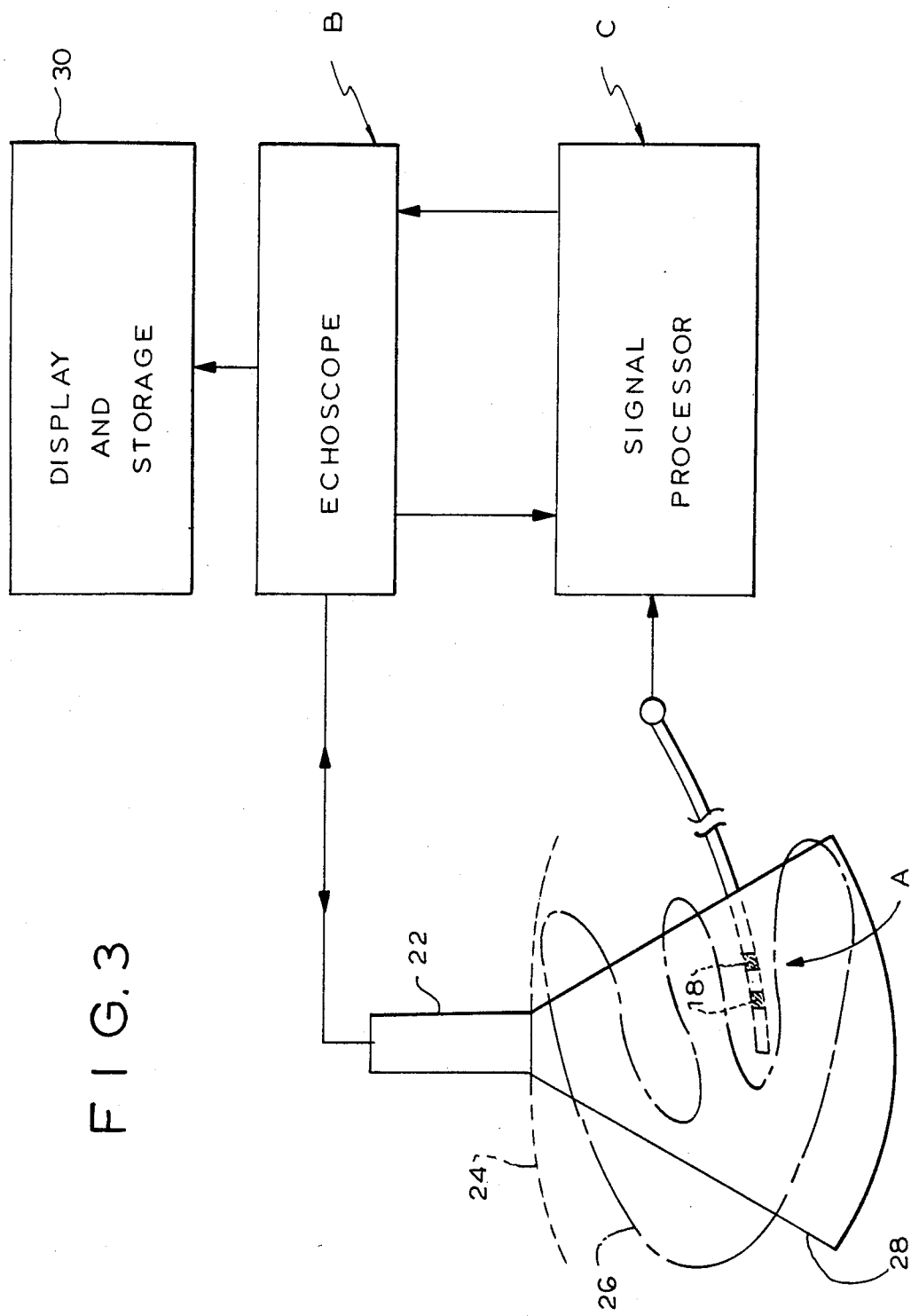

ULTRASONICALLY MARKED CARDIAC CATHETERS

BACKGROUND OF THE INVENTION

The present invention relates to cardiac catheters and, more particularly, to an ultrasonically marked cardiac catheter for use in conjunction with an echocardiograph image display system.

Cardiac catheterization requires the accurate positioning of a catheter within the heart. Since the catheter is not visible, positioning thereof is commonly accomplished through the use of an X-ray system which displays an image depicting the position of the catheter within the body.

However, the use of an X-ray imaging system has various disadvantages. The ionizing radiation is a hazard to the patient and the medical staff. It requires the injection of large volumes of toxic iodine contrast to provide the necessary image clarity. The iodine contrast disturbs the patient's basal haemodynamics and may have toxic effects. It provides only a relatively poor spatial anatomy of the heart. In addition, the equipment required is expensive and requires extensive installation and a large amount of space.

Two-dimensional echocardiography, on the other hand, provides superior spatial anatomy of the heart, involves no irradiation hazard, and requires only small volumes of non-toxic echo-contrast material which does not adversely effect the patient's basal haemodynamics. In addition, the cost of echocardiography equipment is significantly lower than X-ray equipment.

For definitive cardiac diagnosis by ultrasound, intracardiac pressure recording and blood sampling are required for the calculation of intracardiac shunts, in many instances. In order to perform these operations, accurate positioning of the catheter is necessary. When echocardiography is employed, it is necessary that the portions of the catheter in the cardiac cavity be properly marked. Otherwise, accurate catheter positioning is not possible because an unmarked catheter entering or leaving points when intersecting the scanning plane of the echocardiograph can often be misinterpreted as the cathether tip. It is therefore necessary, if an ultrasonic imaging system is to be used for cardiac catheterization, that the catheter be marked in a way that provides an accurate method of determining the position thereof relative to the tissue.

For other types of medical procedures utilizing ultrasound techniques, such as aspiration biopsy, a hollow rigid metal needle has been used through which a point source omnidirectional transducer is inserted. The transducer is electrically connected to the imaging system by wires which extend through the lumen in the needle. Once the needle is properly positioned, the transducer is withdrawn by pulling the wires and, hence, the transducer, back through the needle. After the transducer is withdrawn, the biopsy procedure can take place. This method is, however, not suitable for use in a cardiac catheter because of the rigid metal needle and because the transducer position is not fixed relative to the needle tip and may move relative thereto as the needle is inserted.

It has also been suggested that transducers of various types be permanently mounted within the lumen near the tip or at the base of the needle. However, in such instances, the transducer is necessarily uni-directional, making the apparatus unsuitable for use as a cardiac catheter, even if the needle could be made flexible. Further, a transducer mounted within the needle lumen and the wires connected thereto obstruct fluid flow through the lumen and, therefore, may require separate passageways, resulting in a bulky, difficult to manipulate device.

In general, the present invention overcomes the above problems by providing a cardiac catheter which is flexible and easily manipulatable and which permits accurate omnidirectional positioning through the use of one or more tubular ultrasonic transducers mounted in spaced relation in the wall thereof. Since the transducers and the wire leads therefrom are embedded within the catheter wall, the lumen is unobstructed and the proper electrical isolation is achieved. Because the transducer is embedded in the catheter wall, it is in a fixed position relative to the catheter tip and, thus, accurate positioning of the tip is possible. Because the transducer does not obstruct the lumen, it need not be withdrawn prior to the performance of the medical procedure.

It is, therefore, a prime object of the present invention to provide an ultrasonically marked cardiac catheter.

It is another object of the present invention to provide an ultrasonically marked cardiac catheter which does not require the withdrawal of the ultrasonic marking means prior to the performance of medical procedures.

It is another object of the present invention to provide an ultrasonically marked cardiac catheter wherein one or more ultrasonic transducers are embedded within the catheter wall.

It is another object of the present invention to provide an ultrasonically marked cardiac catheter for use in conjunction with an ultrasonic imaging and display system to permit accurate omni-directional positioning of the catheter tip.

SUMMARY OF THE INVENTION

In accordance with one aspect of the present invention, a catheter is provided comprising a hollow substantially cylindrical wall having an inner surface defining a lumen, an outer surface, and an end. Substantially tubular ultrasonic receiver means are operably mounted in the wall, substantially surrounding a section of the lumen at a fixed position relative to the end. The part of the wall covering the receiver means is designed such as to be substantially transparent to ultrasound. The receiver means is substantially electrically isolated from the inner and outer surface of the wall. The receiver means includes electrical connector means which extend within at least a portion of the length of the wall.

The ultrasonic receiver means preferably comprises first and second ultrasonic receivers. The first and second receivers are operably mounted within the wall at spaced locations along the length thereof. Each ultrasonic receiver means preferably comprises an ultrasonic piezoelectric transducer.

The wall is preferably composed of flexible material, such as plastic. The receiver means is preferably embedded into the wall. The connecting means is also preferably embedded in the wall. The wall itself is preferably comprised of electrically insulating material.

The catheter is preferably a cardiac catheter and is designed for use with ultrasonic imaging and display means. Means are provided which are operably connected to the electrical connecting means for processing signals therefrom. The signal processing means is operably connected to the imaging and display means and provides an output thereto for incorporation into the image display.

To these and to such other objects which may hereinafter appear, the present invention relates to an ultrasonically marked cardiac catheter, as described in the following specification and recited in the annexed claims, taken together with the accompanying drawings, wherein like numerals refer to like parts, and in which:

BRIEF DESCRIPTION OF THE DRAWINGS

FIG. 1 is a side cross-sectional view of a section of the catheter of the present invention;

FIG. 2 is a cross-sectional view taken along line 2—2 of FIG. 1; and

FIG. 3 is a block diagram depicting an ultrasonic imaging and display system with which the catheter of the present invention is adapted for use.

DETAILED DESCRIPTION OF PREFERRED EMBODIMENTS

FIGS. 1 and 2 depict a portion of the tip A of the cardiac catheter of the present invention. The catheter tip includes a body with a hollow substantially cylindrical wall 10. The wall has an inner surface 12 which defines a lumen 14. Wall 10 also has an outer surface 16 and an end 17.

Wall 10 is preferably composed of flexible material, such as plastic, which is substantially ultrasonically transparent at the thickness used herein, as well as being a relatively good electrical insulator. The insulating properties of the catheter wall 10 are important to insure that both patient and medical staff are adequately insulated from the electric signals within the catheter.

Embedded within wall 10 are a plurality (two are shown) of tubular-shaped ultrasonic piezoelectric transducers 18. Piezoelectric transducers are, of course, well known in the art. Such well known transducers can be adapted for use in the present invention by fashioning them into the required tubular shape. Transducers 18 are embedded within wall 10 by any one of a number of known fabrication techniques, including injection molding of the wall 10 around the transducers.

Transducers 18 are permanently positioned relative to end 17. One transducer is preferably located proximate the end 17 as shown. Other ones of the transducers 18 are located at spaced positions along catheter A.

Each transducer 18 has extending therefrom a pair of electrical connecting leads 20. Leads 20 are also preferably embedded within wall 10 and preferably extend within wall 10 along the length of the catheter. The electrical insulating properties of the material from which wall 10 is composed electrically isolate leads 20 from each other and from surfaces 12 and 16 of the catheter.

As is illustrated in FIG. 3, the cardiac catheter of the present invention is designed for use with an echoscope, generally designated B, which utilizes an ultrasonic transducer probe 22. Transducer probe 22 is adapted to be placed over the body of the patient, indicated by dashed lines 24, at a position aligned with the tissue 26 with respect to which catheter tip A is to be positioned. Transducer probe 22 ultrasonically scans a plane 28 by transmitting an ultrasonic pulse in response to a transmit trigger signal from echoscope B, and then generates an electrical receive pulse to echoscope B upon receipt of the echo of the transmitted ultrasonic pulse.

When one of the transducers 18 in tip A is within scanning plane 28, it will receive the ultrasonic pulse transmitted by transducer 22. The transducer 18 will convert the received pulse into an electronic signal which will travel through leads 20 to the input of a signal processor, generally designated C.

Signal processor C is connected to echoscope B so as to also receive the transmit trigger signal which it uses for timing. Signal processor C processes the signal from transducer 18 in a manner which compensates for the fact that the ultrasonic echo received by transducer 22 must travel twice the distance and, hence, requires twice the time, than the ultrasonic signal which is transmitted by transducer probe 22 and received by transducer 18. Signal processor C provides a pulse signal output which is combined with the receive pulse from transducer 22 within echoscope B such that a composite image is provided on the echoscope display 30.

For further details of the operation of signal processor C, the reader is referred to co-pending U.S. patent application Ser. No. 697,059 filed Jan. 31, 1985 in the names of Branko Breyer and Ivo Cikes, and entitled "Signal Processor For Ultrasonically Marked Cardiac Catheter."

It will now be appreciated that the present invention relates to a cardiac catheter which is ultrasonically marked to permit accurate positioning thereof in conjunction with ultrasonic imaging and display equipment. The catheter includes one or more tubular-shaped transducers embedded in fixed positions relative to the end of a flexible plastic wall. The wall is ultrasonically transparent and provides the necessary electrical isolation. The catheter is readily manipulatable and the lumen therein is unobstructed. This permits various medical procedures to be performed easily and safely.

While only a single preferred embodiment of the present invention has been disclosed herein for purposes of illustration, it is obvious that various variations and modifications could be made thereto. It is intended to cover all of these variations and modifications which fall within the scope of the present invention, as defined by the following claims:

1. A catheter comprising a substantially cylindrical wall and a hollow lumen, said wall having an inner surface and an outer surface, said wall being made of an ultrasonically transparent and electrically insulating material, said wall including a substantially tubular ultrasonic receiver means disposed therein, said receiver means spaced from said inner surface and said outer surface of said wall, said receiver means including electrical connector means extending longitudinally within said wall, said receiver means including at least a first and second ultrasonic receiver, said receivers being disposed in said wall at longitudinally spaced positions.

2. The catheter of claim 1, wherein said receivers are ultrasonically piezoelectric transducers.

3. The catheter of claim 1, wherein said catheter is a cardiac catheter.

4. A catheter system comprising:
   a catheter, said catheter including a substantially cylindrical wall and a hollow lumen, said wall having an inner surface and an outer surface, said wall being made of an ultrasonically transparent and electrically insulating material, said wall including at least one ultrasonic receiver means disposed therein, said receiver comprising a single substantially tubular ultrasonic transducer, said receiver spaced from said inner surface and said outer surface of said wall, said receiver including electrical connector means extending longitudinally within said wall;

a signal processing means operably connectable to said electrical connector means; and an imaging and display means for displaying an image, said imaging and display means being operably connectable to said signal processing means, said signal processing means providing an output for incorporation into said image displayed.

5. The system of claim 4, wherein said signal processing means is adapted for processing a signal from an external transducer received by said at least one ultrasonic receiver and for providing a signal representative of the location of said catheter as said output.

6. A cardiac catheter comprising a substantially cylindrical wall and a hollow lumen, said wall having an inner surface and an outer surface, said wall being made of an ultrasonically transparent and electrically insulating material, said wall including a substantially tubular ultrasonic receiver means disposed therein, said receiver means spaced from said inner surface and said outer surface, said receiver means including electrical connector means extending longitudinally within said wall, said receiver means including at least a first and second ultrasonic receiver, said receivers being disposed in said wall at longitudinally spaced positions.

7. The catheter of claim 6, wherein said receivers are ultrasonic piezoelectric transducers.

* * * * *